United States Patent
De Haan

(10) Patent No.: US 12,089,963 B2
(45) Date of Patent: Sep. 17, 2024

(54) SYSTEM AND METHOD FOR DETERMINING AT LEAST ONE VITAL SIGN OF A SUBJECT

(71) Applicant: KONINKLIJKE PHILIPS N.V., Eindhoven (NL)

(72) Inventor: Gerard De Haan, Helmond (NL)

(73) Assignee: Koninklijke Philips N.V., Eindhoven (NL)

( * ) Notice: Subject to any disclaimer, the term of this patent is extended or adjusted under 35 U.S.C. 154(b) by 614 days.

(21) Appl. No.: 17/415,803

(22) PCT Filed: Dec. 11, 2019

(86) PCT No.: PCT/EP2019/084535
§ 371 (c)(1),
(2) Date: Jun. 18, 2021

(87) PCT Pub. No.: WO2020/126713
PCT Pub. Date: Jun. 25, 2020

(65) Prior Publication Data
US 2022/0047221 A1 Feb. 17, 2022

(30) Foreign Application Priority Data
Dec. 19, 2018 (EP) ..................... 18213865

(51) Int. Cl.
*A61B 5/00* (2006.01)
*A61B 5/024* (2006.01)

(52) U.S. Cl.
CPC ........ *A61B 5/7228* (2013.01); *A61B 5/02433* (2013.01); *A61B 5/7207* (2013.01)

(58) Field of Classification Search
CPC .. A61B 5/02433; A61B 5/7228; A61B 5/7207
See application file for complete search history.

(56) References Cited

U.S. PATENT DOCUMENTS

| 8,768,424 | B2 | 7/2014 | Crowe | |
|---|---|---|---|---|
| 2008/0077015 | A1* | 3/2008 | Boric-Lubecke | ..... G01S 13/888 600/453 |

(Continued)

FOREIGN PATENT DOCUMENTS

| WO | 2013190423 A1 | 12/2013 |
|---|---|---|
| WO | 2017137415 A1 | 8/2017 |
| WO | 2018029127 A1 | 2/2018 |

OTHER PUBLICATIONS

W. Wang et al., "Algorithmic Principles of Remote-PPG", IEEE Transactions on Biomedical Engineering, vol. 64, No. 7, Jun. 15, 2017.

(Continued)

*Primary Examiner* — Joel F Brutus

(57) ABSTRACT

The present invention relates to a system and method for determining a vital sign of a subject. To improve the detection of electromagnetic radiation reflected from or transmitted through skin of a subject (110) at least two differently modulated radiation sources (112, 114) are used. For both camera and single-element sensors, this allows access (after demodulation) to different mixtures of skin and non-skin reflections/transmissions that can be de-mixed and successively allows the skin-only signal to be used for photo-plethysmography, PPG, extraction. Thus, a sensor (130) detects the reflected or transmitted electromagnetic radiation and a demodulation unit (140) and processing unit (150) enable to determine a vital sign (160) from said detection signal.

15 Claims, 5 Drawing Sheets

(56) References Cited

U.S. PATENT DOCUMENTS

| | | | |
|---|---|---|---|
| 2009/0306487 A1 | 12/2009 | Crowe | |
| 2012/0065714 A1* | 3/2012 | Szasz | A61N 1/403 |
| | | | 607/101 |
| 2012/0108928 A1 | 5/2012 | Tverskoy | |
| 2013/0303921 A1 | 11/2013 | Chu | |
| 2014/0194793 A1* | 7/2014 | Nakata | G01S 13/87 |
| | | | 601/48 |
| 2014/0275832 A1* | 9/2014 | Muehlsteff | A61B 5/6889 |
| | | | 600/301 |
| 2015/0126872 A1* | 5/2015 | Dubielczyk | A61B 5/682 |
| | | | 600/476 |
| 2016/0095524 A1 | 4/2016 | Estepp | |
| 2016/0120482 A1* | 5/2016 | Kirenko | A61B 5/7278 |
| | | | 600/479 |
| 2016/0302679 A1* | 10/2016 | De Haan | A61B 5/1455 |
| 2017/0095170 A1* | 4/2017 | Verkruijsse | A61B 5/02416 |
| 2017/0224246 A1 | 8/2017 | Jiang | |
| 2017/0325699 A9 | 11/2017 | Vermeulen et al. | |

OTHER PUBLICATIONS

M. Van Gastel, S. Stuijk and G. De Haan, "New Principle for Measuring Arterial Blood Oxygenation, Enabling Motion-Robust Remote Monitoring", Nature Scientific Reports, Nov. 2016.
International Search Report Jan. 30, 2020.

\* cited by examiner

SYSTEM AND METHOD FOR DETERMINING AT LEAST ONE VITAL SIGN OF A SUBJECT

CROSS-REFERENCE TO PRIOR APPLICATIONS

This application is the U.S. National Phase application under 35 U.S.C. § 371 of International Application No. PCT/EP2019/084535, filed on Dec. 11, 2019, which claims the benefit of European Application No.18213865.1 filed on Dec. 19, 2018. These applications are hereby incorporated by reference herein.

FIELD OF THE INVENTION

The present invention relates to a system and method for determining at least one vital sign of a subject

BACKGROUND OF THE INVENTION

The determination of vital signs of a person serve as indicators of the current state of the person and enable improved/timely medical treatments, which is of particular relevance, e.g., in hospitals, but also at home or in further health, leisure and fitness settings.

One way of measuring vital signs is plethysmography. This technique has been established to measure vital signs, such as the heart rate (HR), the respiration rate (RR) or the (peripheral or pulsatile) blood oxygen saturation (SpO2). The underlying idea of this technique is the measurement of volume changes of an organ or body part, wherein the volume change is modulated with every heartbeat of the person.

An optically obtained plethysmography, is called photoplethysmography (PPG), and has gained more and more interest in recent years. A well-known way of obtaining such a PPG is by using a pulse oximeter, which illuminates the skin and measures changes in light absorption. The optical measurement technique, either performed in transmission or reflection mode, typically uses visible or infrared radiation due to the large penetration depth of this particular electromagnetic radiation in skin and tissue. The absorption of blood, for these wavelengths, is larger than the absorption of the surrounding tissue. Thus, the variations in blood volume during the cardiac cycle affect the transmission or reflection correspondingly and enable to extract vital signs such as the pulse rate (heart rate). The blood oxygen saturation (SpO2) can be determined by evaluating the transmittance and/or reflectance of electromagnetic radiation with different wavelengths, whereby a combination of red and infrared radiation is typically used.

Conventional PPG devices, such as the mentioned pulse oximeter, are attached to the skin of the subject, for instance to a fingertip. Others may be attached, e.g., to the earlobe or forehead. This technique has been established in the field of medical treatment, but also has its specific disadvantages. Some patients regard the technique as being unpleasant and obtrusive, since the device, such as the oximeter, is directly attached to the subject and any cables limit the freedom to move and might hinder the workflow of the patient as well as of the medical aide.

For some patients, the contact devices are not only unpleasant, but also inappropriate. This is the case for patients with fragile skin, such as babies in the neonatal intensive care unit. These patients highly benefit from contactless optical monitoring of vital signs, which is called remote photoplethysmography (rPPG). The rPPG devices and systems are unobtrusive and well suited for medical as well as non-medical applications. Electromagnetic radiation is transmitted through or reflected from a patient and detected by a sensor. The detected signal is further processed to extract the vital signs based on the small modulations in skin reflectance or transmission.

A disadvantage of rPPG compared to conventional contact PPG is that the rPPG signal strength is lower and the detection and tracking of a suitable skin area of the subject being monitored is challenging, especially by taking into account that patients, such as babies, regularly move. Without thinking about improved techniques referring, e.g., to the illumination technique, the filtering of the signal or the proper skin detection, the signals of rPPG are often not valuable as these are full of noise, which results from various sources, such as the background illumination or the reflected/transmitted signal from non-skin parts of the patient. Thus, there is a need for an improved system and method for determining at least one vital sign of a subject to obtain results with high reliability, even in case of noise and/or motion.

US 2009/0306487 A1 discloses a method and apparatus for measuring pulse rate, breathing rate and blood constituents by using PPG. A modulated PPG device that should improve reliability through the reduction of noise when the PPG device is used in transmission mode. In addition, the choice of light in the blue/green portion of the optical spectrum should give improved reliability through the reduction of noise and the increase in AC component signal amplitude, when the PPG device is used in reflection mode.

SUMMARY OF THE INVENTION

It is an object of the present invention to provide a system and method for determining a vital sign of a subject with increased PPG signal due to improved detection and tracking of suitable skin area of the subject being monitored.

In a first aspect of the present invention a system for determining a vital sign of a subject is presented comprising
  two radiation sources emitting differently modulated electromagnetic radiation with substantially the same emission spectrum having at least one equivalent wavelength onto a scene including the subject from different directions;
  a sensor for detecting the electromagnetic radiation from a scene including the subject and for deriving a detection signal from the detected electromagnetic radiation;
  a demodulation unit configured to demodulate the detection signal to obtain two demodulated signals, each being demodulated differently using a demodulation corresponding to one of the modulations used for modulating the electromagnetic radiation emitted by one of said two radiation sources; and
  a processing unit configured to
    determine a vital sign of the subject by combining information from said two demodulated signals,
    demix the demodulated detection signal into a skin signal representing mainly electromagnetic radiation transmitted through or reflected from the skin of the subject and a non-skin signal representing mainly electromagnetic radiation not transmitted through or reflected from the skin of the subject, and
    determine a vital sign of the subject from said skin signal.

In a further aspect of the present invention, a corresponding method is presented.

Preferred embodiments of the invention are defined in the dependent claims. It shall be understood that the claimed method has similar and/or identical preferred embodiments as the claimed system, in particular as defined in the dependent claims and as disclosed herein.

One main problem solved by the present invention is a returning issue of remote PPG technique, the detection and tracking of a suitable skin area of the subject being monitored. Prior art camera-based techniques choose a skin area from the subject to extract the PPG signal. Typically face detection or some form of skin color segmentation is being used. Color segmentation is problematic in near infrared (NIR), where contrasts are often marginal, while face detection techniques generally assume visibility or facial features, which is often problematic in health-care settings where patients may wear masks or have tubes inserted in mouth or nose. Furthermore, camera-based methods need to, at least partially, image the subject without guarantee that this image cannot be viewed by another person, which raises privacy concerns.

An essential element of the current invention to overcome said problem is to illuminate a scene including a subject inhomogeneously. Thus, different radiation sources irradiating the scene under different angles and modulated differently (e.g., different frequency or phase) are used. For both camera and single-element sensors, this allows access (after demodulation) to different mixtures of skin and non-skin reflections that can be de-mixed and successively used for PPG extraction. Particularly for the single element detector this offer is a unique opportunity to (maybe not completely, but at least partially) separate the skin and non-skin reflection in the detector signal. For cameras alternatives may exist, like segmentation, but these often are far from trivial, particularly in the NIR range of the spectrum.

The two radiation sources are not only configured to illuminate a scene including a subject from different directions and differently modulated, but further with substantially the same emission spectrum having at least one equivalent wavelength. Hence, the emission spectrum emitted by a first radiation source and the emission spectrum emitted by a second radiation source comprise at least one equivalent wavelength, i.e., both spectra overlap. In said context, at least one equivalent wavelength means that the spectra may even comprise several equivalent wavelengths or one or more overlapping (equivalent) wavelength ranges.

In this context, it shall be noted that the term "vital sign" shall be understood broadly in the sense of "physiological parameter" including not only vital signs in the strict sense, but also other physiological parameters like SvO2 or SaO2. The processing unit may thus be configured to determine as vital sign an indicator or concentration of blood components or species, in particular SpO2, SvO2, HBO2, HBCO, METHB, Bilirubin, and wherein the pulsatile component reflects the cardiac cycle or the respiratory cycle.

In the case of a reflection setup the radiation detected by the sensor may result from reflections of non-skin parts of the subject, such as the clothes and hair, as well as from the surrounding environment, e.g. the background of the subject. A skin signal representing mainly electromagnetic radiation transmitted through or reflected from the skin of the subject means in this context that the major contribution of the electromagnetic radiation is transmitted through or reflected from the skin of the subject. Accordingly, a non-skin signal has a major contribution of non-skin parts.

In particular, the variations (AC-part) of the skin-reflection signal represent, or can be used to derive the vital sign. For example, it requires (accurate) AC/DC estimates at multiple wavelengths for the skin-regions to enable a reliable extraction of SpO2, while the AC-variation themselves corresponds with a pulse signal, from which furthermore a pulse-rate may be derived In another embodiment, the processing unit is configured to use a blind-source separation (BSS), in particular Independent Component Analysis (ICA) and/or Principal Component Analysis (PCA) to demix the demodulated detection signals into a skin signal and non-skin signal, wherein the skin signal is selected by use of a quality metric, in particular spectral flatness, skewness, highest peak in normalized FFT spectrum and/or signal-to-noise ratio. This embodiment exploits the fact that the reflected or transmitted radiation contains a mixture of the two differently modulated electromagnetic radiations; each containing a different mix of radiation reflected from or transmitted through skin and non-skin parts. The BSS then uses a similar or a different criterion or quality metric to separate different RGB traces into uncorrelated or independent signal sources to retrieve the pulse. The application of BSS-based methods, for this purpose, is further explained, e.g., in W. Wang et al. "Algorithmic principles of remote-PPG", IEEE Transactions on Biomedical Engineering", 64(7), 1479, 2017.

The radiation sources are configured to emit electromagnetic radiation with substantially the same optical spectrum in a range from 400 nm to 1000 nm. The VIS and NIR range is ideally suited for determining vital signs and, preferably, the radiation sources each comprise one or more radiation elements to emit electromagnetic radiation with different sub-spectra. The combined sub-spectra of these radiation elements form the emission spectrum of the radiation sources with an optical spectrum that is, preferably, in a range from 400 nm to 1000 nm. Thus, a LED-combination may be used with multiple wavelengths to irradiate the scene, e.g., a blue LED emitting at 450 nm, a green LED emitting at 550 nm and a red LED emitting at 650 nm. According to this embodiment, the emitted light of the radiation sources is perceived as "white" light by a subject.

According to such kind of embodiment, where the radiation sources each comprise one or more radiation elements, the processing unit is configured to combine skin signals corresponding to electromagnetic radiation emitted with one sub-spectrum by the radiation elements with skin signals corresponding to electromagnetic radiation with another sub-spectrum emitted by the radiation elements by using any one of chrominance based methods, CHROM, blood volume pulse, PBV, plane orthogonal to skin, POS, or adaptive blood volume pulse, APBV, to extract a vital sign from the skin signals. Such sub-spectra are not necessarily emitted by separate radiation elements, but may result from sensors equipped with different optical filters using radiation emitted from a wide-range (e.g., white sun-light) radiation source.

Details of these methods are described in W. Wang et al. "Algorithmic principles of remote-PPG", IEEE Transactions on Biomedical Engineering", 64(7), 1479, 2017 and M. van Gastel, S. Stuijk and G. de Haan "New principle for measuring arterial blood oxygenation, enabling motion-robust remote monitoring", Scientific Reports, 6, 38609, 2016 and also partly herein incorporated by reference. CHROM is a very reliable method, though applicable particularly for visible light (400-700 nm), and bases on the linear combination of the chrominance-signals by assuming a standardized skin-color to white balance, whereas PBV is applicable to all wavelength-choices and uses the signature of blood volume changes in different wavelengths to explicitly distinguish the pulse-induced color changes from motion noise in RGB measurements. This wavelength-dependency of the PPG signal varies when the composition of blood changes.

In particular, it is strongly affected by the oxygen saturation of the arterial blood. This dependency can be used to realize a motion-robust remote SpO2 monitoring system that has been named adaptive PBV method (APBV) and is described in detail in M. van Gastel, S. Stuijk and G. de Haan, "New principle for measuring arterial blood oxygenation, enabling motion-robust remote monitoring", Nature Scientific Reports, Nov. 2016. The plane orthogonal to skin (POS) defines a plane orthogonal to the skin-tone in the temporally normalized RGB space, which is used for pulse extraction.

In an embodiment, the radiation sources are configured to emit amplitude modulated electromagnetic radiation. The amplitude modulation of each radiation source uses different frequency and/or phase modulation. This results in a different frequency/phase multiplex of the detected signals by the sensor that can consequently be demultiplexed/demodulated.

In a specific embodiment, where the sensor for detecting the electromagnetic radiation is a camera and the differently modulated radiation emitted by the two radiation sources is amplitude modulated using different frequencies, the different modulating frequencies differ more than the maximum frequency of a periodic vital sign and the highest modulating frequency is less than half the picture-rate of the optical sensor minus the maximum anticipated pulse-rate. Thus, the difference of the modulating frequencies is properly chosen to reliably resolve the time dependency of the vital signs by considering the camera's picture rate. In a particular embodiment, one of the modulating frequencies may be 0 Hz, i.e. in this case one of the radiation sources is emitting continuous radiation, while the other emits a time-varying radiation. This particular option allows the use of ambient light (e.g. sunlight) as one of the radiation sources.

According to another embodiment, the radiation sources are configured to emit electromagnetic radiation that has been modulated with the same frequency, but uses a phase offset. This may be achieved by installing a time delay for delaying one of the modulation signals that determines the strength of the electromagnetic radiations with respect to the modulation signal that modulates the other radiator.

In general, the modulation resulting in, either frequency or phase multiplexing, is used to reduce noise in the detected signal as well as allow separating the detected signal into contributions of the different radiation sources. This is achieved by the demodulation unit.

Preferably, the demodulation unit comprises one or more amplitude modulated (AM) demodulators configured to output a number of output signals according to the number of radiation sources. The demodulation unit may particularly comprise different demodulates for the differently modulated source signals. It may be advantageous to use more than two differently modulated radiation sources illuminating the scene under different angles, as this allows separation of more independent components that may occur, e.g., due to motions in the scene. Thus, using more than two radiation sources allows getting signals with an improved signal-to-noise ratio, but also increase the computational burden.

According to another embodiment, the demodulating unit is further configured to normalize and/or band-pass filter the demodulated signal to limit the frequency range of the demodulated signal to the relevant frequencies of the determined vital sign, wherein normalization of the demodulated signal involves dividing each signal by its temporal mean or taking a logarithm of the demodulated signal. Possibly, the logarithm is taken after correction for the combination coefficients in the extraction.

The BSS leads to a weighting of the individual sensor signals, whereby each sensor signal is corresponding to the transmission or reflection of the emitted electromagnetic radiation of different radiation sources. This weighting uses combination coefficients (one for each radiation source). Consequently, the contribution of reflection or transmission from each radiation source to the signal depends on these combination coefficients. The logarithm as well as the normalization may correct for these combination coefficients.

According to another embodiment, the demodulation unit further comprises a synthetic waveform generator, wherein the radiation sources are frequency multiplexed with sinusoidal waveforms and wherein the demodulation unit is configured to recover the modulating waveforms from the detected signal by detecting the modulating frequencies of the detected signal and generating analytic signals using the synthetic waveform generator that produces sinusoidal waveforms with a fixed amplitude and the detected frequencies.

BRIEF DESCRIPTION OF THE DRAWINGS

These and other aspects of the invention will be apparent from and elucidated with reference to the embodiment(s) described hereinafter. In the following drawings

DETAILED DESCRIPTION OF EMBODIMENTS

Figure 1:
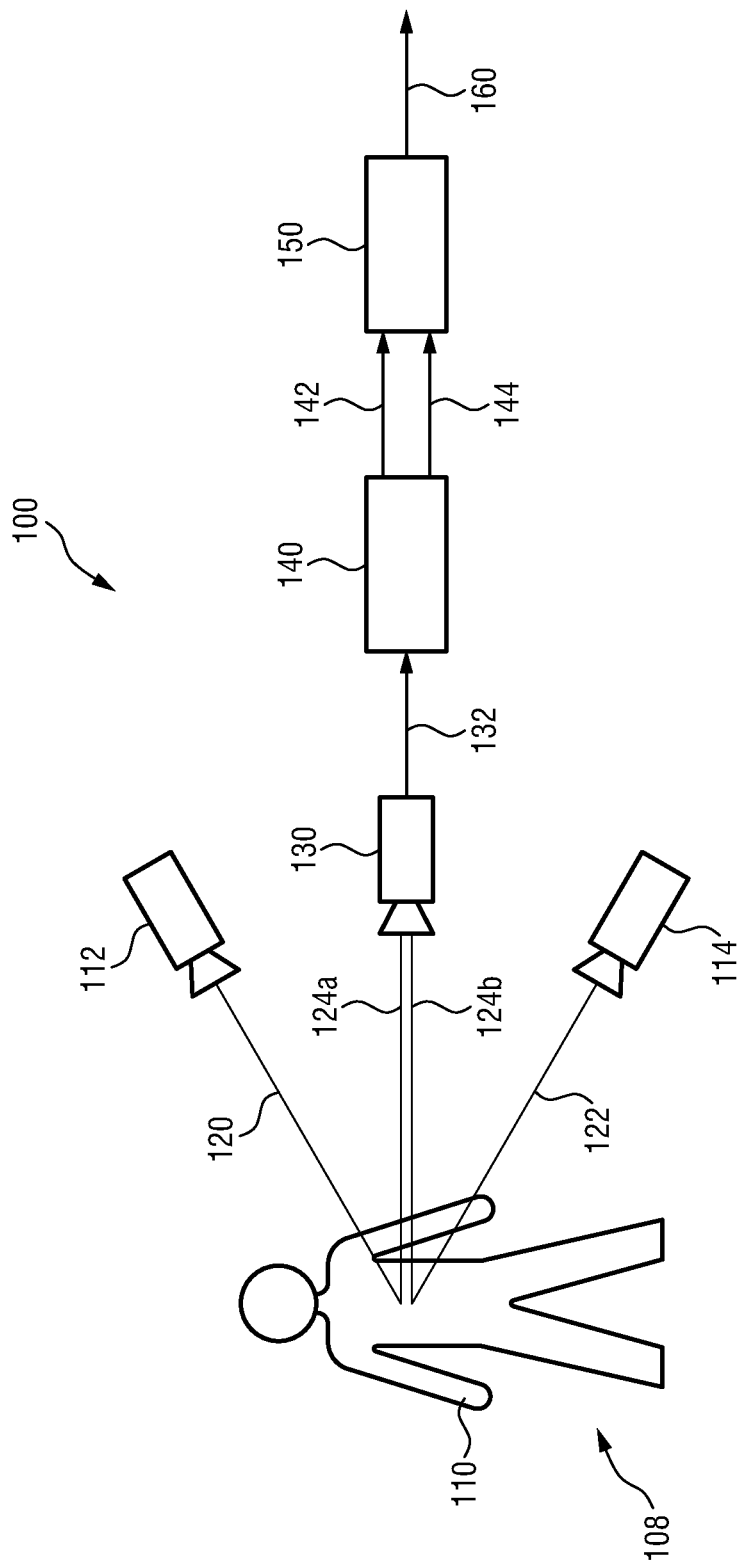
FIG. 1 shows a schematic diagram of a first embodiment of a system according to the present invention.

FIG. 1 shows a schematic diagram of a first embodiment of a system 100 according to the present invention. The system 100 comprises two radiation sources 112, 114 that emit differently modulated electromagnetic radiation with substantially the same emission spectrum. A detailed description of the modulation process is given later with reference to FIG. 2.

The radiation sources 112, 114 are arranged at different positions with respect to the subject 110 and irradiate the scene 108 including the subject 110 from different angles. The electromagnetic radiation 120, 122 emitted by the radiation sources 112, 114 gets reflected at the subject 110 and the surrounding environment of the subject 110 according to this embodiment. Thus, it may also be a viable option that one of the radiation sources 112, 114 illuminates the background and the other radiation source 114, 112 substantially illuminates the subject 110. Subsequently, the reflected electromagnetic radiation 124a, 124b is detected by a sensor 130. The sensor 130 may be a single element detector, e.g., a photodiode, a sensor array, e.g., an 8×8 photo-sensor array, a line-sensor array or an image sensor (e.g. a camera).

Preferably, at least one of the radiation sources 112, 114 and the sensor 130 are arranged such that the reflected electromagnetic radiation 124a, 124b contains a large contribution of radiation reflected from the skin of the subject. To determine the location of skin in the scene 108 various techniques may be used including skin color or thermal information (skin is typically warmer than textiles and other objects) to automatically realign the radiations sources 112, 114 and the sensor 130 with respect to the subject. Alternatively, e.g. in a static setup (e.g. monitoring a driver in a car or a patient in a bed) using an image sensor, skin detection may be used and parts of the scene may be neglected using this information. Thus, only image processing means are applied to determine the location of the skin.

A problem solved by the present invention is that the reflected electromagnetic radiation 124a, 124b typically further contains some contribution of non-skin signals representing electromagnetic radiation not reflected from the skin of the subject 110. Thus, this particular electromagnetic radiation is reflected, e.g., at clothes and hair of the subject 110 or at any kind of object located close to the subject. The scene 108 is typically at least not completely static as the subject 110 moves which leads to constantly varying skin contribution in the reflected electromagnetic radiation 124a, 124b. Hence, the difficulties threatening the viability of camera-based PPG are robustness to subject movements and finding the actual skin of the subject 110. Various options have been researched recently and the essential element of the present invention to overcome said problem is to illuminate the scene inhomogeneously by using at least two differently modulated radiation sources 112, 114 as it is shown in FIG. 1.

According to a preferred embodiment the radiation sources 112, 114 are configured to emit electromagnetic radiation 120, 122 with substantially the same optical spectrum (as observed by the sensor) in a range from 400 nm to 1000 nm as the visible (VIS) and near infrared (NIR) range is well known to be ideally suited for unobtrusive measurements of pulse, respiration, SpO2, etc.

Figure 2:
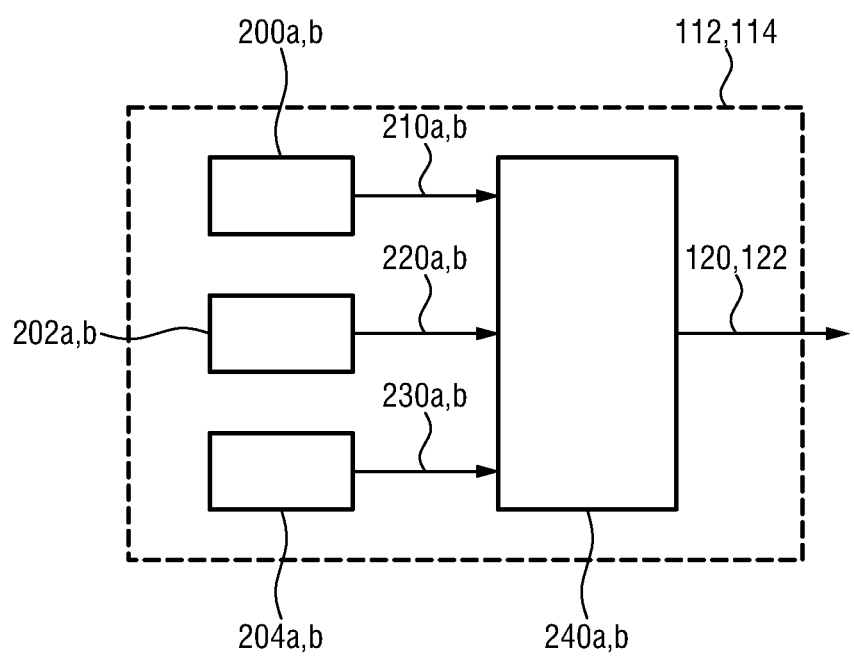
FIG. 2 shows a schematic diagram of the radiation sources according to one embodiment.

FIG. 2 shows a schematic diagram of the radiation sources 112, 114 according to an embodiment, where the radiation sources 112, 114 each comprise one or more radiation elements 200a,b, 202a,b, 204a,b to emit electromagnetic radiation with sub-spectra and wherein the combined sub-spectra of the radiation elements 200a,b, 202a,b, 204a,b form the emission spectrum of the radiation sources 112, 114. In case of this embodiment the radiation elements 200a,b, 202a,b, 204a,b may be different light emitting diodes (LEDs) and it can be advantageous to choose wavelengths between 400 nm and 1000 nm, e.g., [450 nm, 550 nm, 650 nm] or [760 nm, 800 nm, 880 nm]. The first combination results from a blue, green and red LED. Hence, the electromagnetic radiation 120, 122 emitted by the radiation sources 112, 114 is white light, which is a mixture of the sub-spectra of the single LEDs. Furthermore, it is advantageous to choose wavelength close to 550 nm as the PPG-spectrum shows the highest amplitude there.

It should be noted that only one exemplary embodiment of the radiation sources 112, 114 is shown in FIG. 2. The radiation sources 112, 114 may comprise, in general, even more LEDs as this allows separation of more independent components that may occur, e.g., due to motions in the scene. Furthermore, the radiation sources 112, 114 may emit a wide optical spectrum (e.g., white LED) and the elements of the sensor 130 select different sub-spectra from this wide spectrum (e.g., red, green and blue pixels).

The emitted electromagnetic radiation 210a,b, 220a,b, 230a,b of the different radiation elements 200a,b, 202a,b, 204a,b may be unmodulated electromagnetic radiation 210a,b, 220a,b, 230a,b which passes a modulation unit 240a,b in order to modulate the electromagnetic radiation. More advantageously, the radiation elements 200a,b, 202a, b, 204a,b directly emit modulated electromagnetic radiation as their drivers steer a modulated current through each of them. The modulation unit 240a,b may be an amplitude modulation unit, and the different radiation elements 200a,b, 202a,b, 204a,b are modulated with a different frequency or phase, resulting in a frequency or phase multiplexed electromagnetic radiation. In case of a phase modulation, the modulation unit 240a,b may be a time delay unit, which delays one of the electromagnetic radiation 120, 122 with respect to the other, or may use time-multiplexing or quadrature modulation.

According to another embodiment, the modulation signal that drives the current of the radiation elements 200a,b, 202a,b, 204a,b is delayed for one of the radiation sources 112, 114 with respect to the other radiation source 112, 114. In case of a frequency multiplexing, the modulation unit 240a,b may be, e.g., an optical chopper wheel or an acousto-optic modulator (AOM). A more attractive, and cheaper embodiment may also be here to modulate the radiation elements 200a,b, 202a,b, 204a,b directly instead of assuming a continuous radiator and a modulation unit 240. The frequency of the modulation is adjusted properly to effectively reduce noise in the PPG signal, which results from various sources such as the ambient light source, other electrical apparatuses or the electrical noise of the PPG signal itself. It may be advantageous to modulate the electromagnetic radiation with sinusoidal waveforms, where the modulating frequencies of the two radiation sources 112, 114 differ more than the maximum frequency of a periodic vital sign (e.g., the maximum pulse frequency, i.e. 4 Hz) and wherein the highest modulating frequency is less than half the picture-rate of the optical sensor minus the maximum anticipated pulse-rate. Thus, the radiation sources 112 and 114 are each modulated with a different frequency, e.g., at 1 kHz and 1.2 kHz, where the difference of the modulating frequencies fulfils said requirement. Furthermore, it is highly beneficial to choose a frequency range which differs from the typical frequencies of the mentioned noise sources to effectively filter the signal by the modulation and demodulation process.

According to another embodiment, the radiation sources 112, 114 are amplitude modulated with two sinusoidal waveforms between 0% and 99% of the maximum output, e.g., 20%, and the maximum light-output (100%).

It should also be noted that "differently modulated radiation sources" covers the case where one of the radiation sources 112, 114 is modulated, e.g., at 1 kHz, while the other radiation source 112 or 114 is modulated at 0 kHz.

As already mentioned above, the electromagnetic radiation 120, 122 emitted by at least one of the two radiation sources 112, 114 is reflected at the subject as it is shown in the schematic diagram in FIG. 1. The reflected electromagnetic radiation 124a, 124b is detected by an optical sensor, which may be, e.g., a photo-diode that has a plurality of elements sensitive to blue, green, red and near-infrared radiation. Thus, if the radiation sources 112, 114 emit white light, which is decomposed into a blue, green and red sub-spectrum of the radiation elements 200a,b, 202a,b, 204a,b (see FIG. 2), the different RGB sensors may have the same relative strength. However, this is not necessary, as long as their outputs are high enough to achieve a good signal-to-noise ratio.

The sensor 130 converts the reflected electromagnetic radiation 124a, 124b into a detection signal 132, which is transferred to the demodulation unit 140. Preferably, the demodulation unit 140 is an amplitude (AM) demodulator configured to output a number of output signals according to the number of radiation sources. According to the embodiment presented in FIG. 1, the number of radiation sources 112, 114 is two. However, it will be explained later with reference to FIG. 5 that the claimed system may comprise even more radiation sources.

Figure 3:
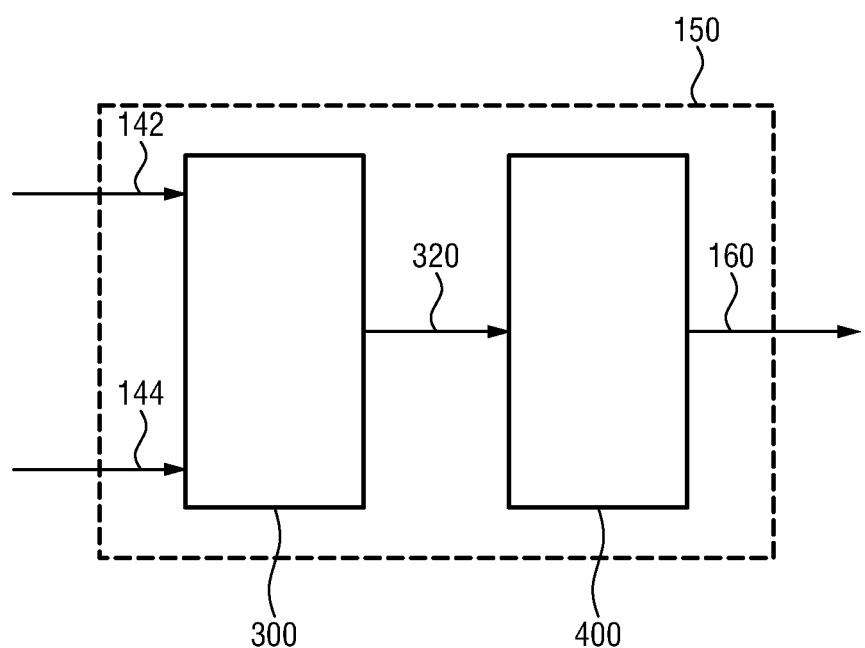
FIG. 3 shows a schematic diagram of the processing unit according to one embodiment.

In case of the embodiment shown in FIG. 1, the demodulation unit 140 "recovers" two demodulated signals 142, 144 that correspond to the differently modulated electromagnetic radiation 120, 122 of the two radiation sources 112, 114. Particularly, it allows extracting the variations (AC-part) of the skin signal representing the vital sign. The demodulation unit 140 may operate in an overlap-add fashion, where the output signal is reconstructed by adding the evaluated overlapping time series. Said demodulated signals 142, 144 are transferred to the processing unit 150. One embodiment of the processing unit is shown in FIG. 3.

According to this embodiment the processing unit 150 further comprises a separation unit 300, where a blind-source separation (BSS), e.g., Independent Component Analysis (ICA) and/or Principal Component Analysis (PCA), is used to separate the two demodulated signals 142, 144 into a skin signal 320 and a non-skin signal, wherein (as a preferred option) only the relevant skin signal 320 is further processed and sent to the determination unit 400 that is configured to extract the final vital signs 160 from the skin signal 320. The skin signal 320 is a linear combination of the electromagnetic radiation 120, 122 emitted by the two radiation sources 112,114 and substantially transmitted through or reflected by the skin of the subject 110. According to an alternative option (e.g., assuming RGB sub-spectra and two radiators) all six (2×3) signals may be fed into a BSS-unit for separation of the pulse signal.

The general procedure of BSS-based methods applied in rPPG can be expressed as $Y(t)=A \cdot X(t)$, where $Y(t)=(Y1, Y2)^T$ denotes the factorized source-signals consisting of the pulse and noise. Thus, in the specific embodiment shown in FIG. 3 the first demodulated signal 142 corresponds, e.g., to the reflected electromagnetic radiation 120 emitted by the first radiation source 112 and the second demodulated signal 144 corresponds to the reflected electromagnetic radiation 122 emitted by the second radiation source 114, wherein both radiation sources 112, 114 emit with substantially the same emission spectrum. The vector $X(t)=(X1, X2)^T$ denotes the de-mixed signal, wherein X1 is the skin signal 320 and X2 the non-skin signal, which is not used for further processing. A denotes the de-mixing matrix that can be estimated by ICA or PCA to separate the demodulated signals 142, 144 into a skin signal 320 and non-skin signal.

Figure 4:
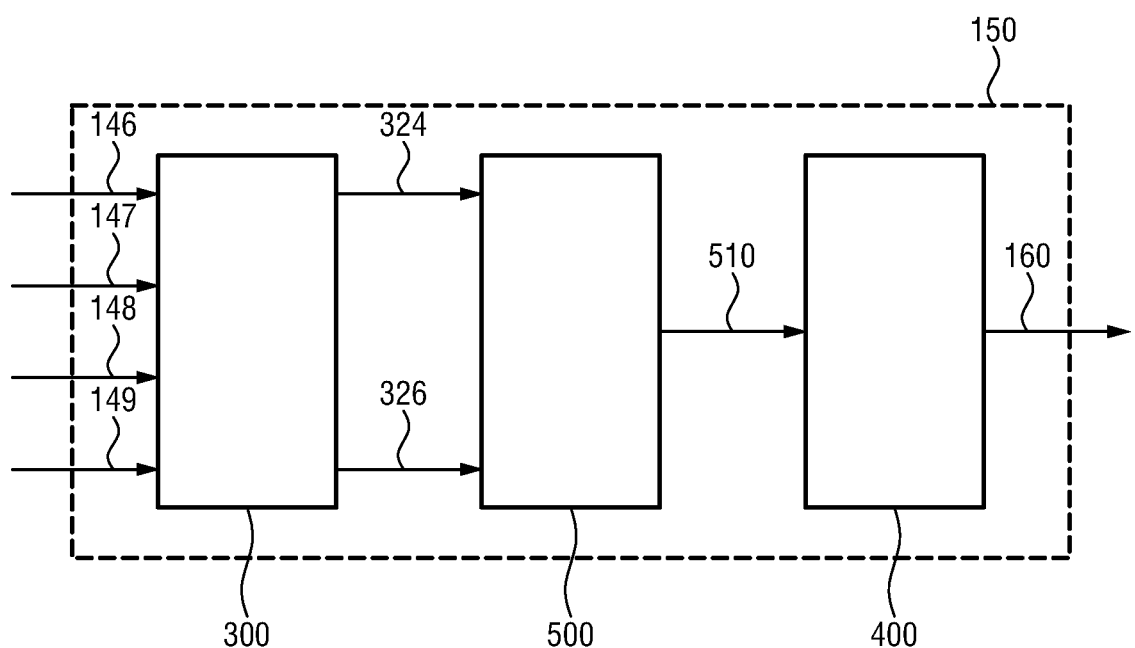
FIG. 4 shows a schematic diagram of the processing unit according to another embodiment.

According to another embodiment shown in FIG. 4, the radiation sources 112, 114 do not only emit with substantially the same emission spectrum, but also comprise further radiation elements as described for the embodiment shown in FIG. 2. Thus, the radiation sources 112, 114 may, e.g., further comprise two radiation elements, respectively, that emit with a center wavelength of $\lambda 1$ and $\lambda 2$. Hence, the radiation sources 112, 114 may be configured to emit with the same emission spectrum as the emission spectrum is formed from the combined sub-spectra of the radiation elements. In that case the first demodulated signal 146 corresponds, e.g., to the reflected electromagnetic radiation emitted by the first radiation element 200a of the first radiation source 112, the second demodulated signal 147 corresponds to the reflected electromagnetic radiation emitted by the second radiation element 202a of the first radiation source 112, the third demodulated signal 148 corresponds to the reflected electromagnetic radiation emitted by the first radiation element 200b of the second radiation source 114 and the fourth demodulated signal 149 corresponds to the reflected electromagnetic radiation emitted by the second radiation element 202b of the second radiation source 114. It is assumed exemplary that the first radiation elements 200a,b emit electromagnetic radiation with a center wavelength of $\lambda 1$, whereas the second radiation elements 202a,b emit electromagnetic radiation with a center wavelength of $\lambda 2$. It should be noted at that point that the present invention is not limited to electromagnetic radiation with two different center wavelengths $\lambda 1$ and $\lambda 2$. More than two are a viable option.

The separation unit 300 uses a blind-source separation (BSS), e.g., Independent Component Analysis (ICA) and/or Principal Component Analysis (PCA), to separate the four demodulated signals 146-149 into a first skin signal 324 corresponding to electromagnetic radiation with a center wavelength of $\lambda 1$, a second skin signal 326 corresponding to electromagnetic radiation with a center wavelength of $\lambda 2$ and two non-skin signals. As shown in FIG. 4, the first skin signal 324 and the second skin signal 326 enter a combination unit 500, where chrominance based method (CHROM), blood volume pulse (PBV), plane orthogonal to skin (POS) or adaptive blood volume pulse (ABPV) are used to combine the skin-reflected signals in different wavelengths. This combined skin-signal 510 is then transferred to the determination unit 400 that is configured to extract the final vital signs 160 from the combined skin signal 510.

Figure 5:
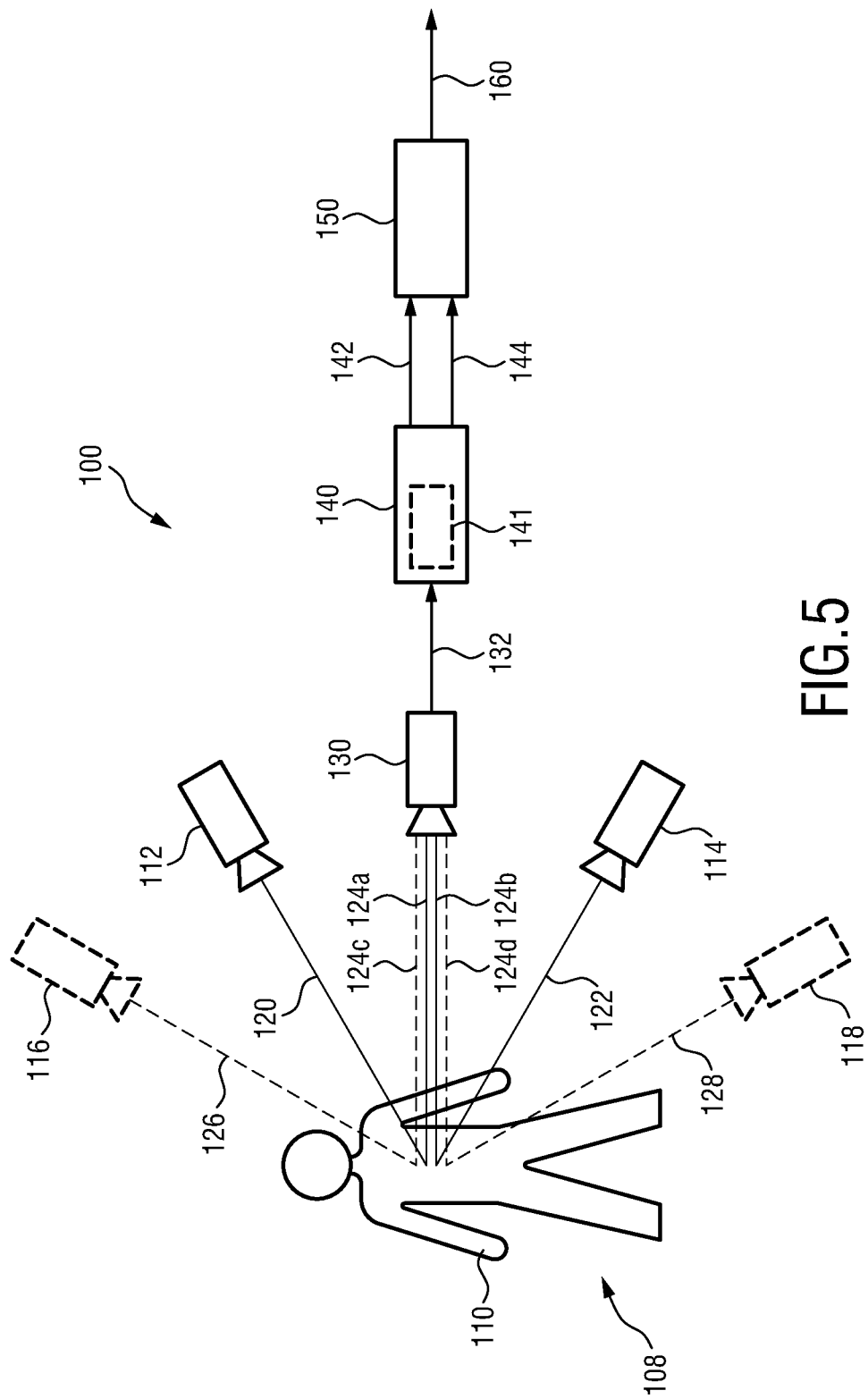
FIG. 5 shows a schematic diagram of a second embodiment of the system according to the present invention.

FIG. 5 shows another embodiment of the system 100 according to the present invention for determining at least one vital sign of a subject 110. As already mentioned above, the system 100 may comprise even more radiation sources 112, 114, 116, 118, . . . . It may be advantageous to use more than two differently modulated radiation sources 112, 114, 116, 118, . . . to illuminate the scene 108 under different angles, as this allows separation of more independent components that may occur, e.g., due to motions in the scene 108. According to this embodiment with four radiation sources 112, 114, 116, 118, the reflected electromagnetic radiation of the subject 124a-d is processed in the same way as it has already been described for the embodiment shown in FIG. 1. The only difference is that there exist two more differently modulated electromagnetic radiations 126, 128 that have to be processed. Thus, the computational burden is larger, but it may be of interest in order to get an improved quality of the determined vital signs 160.

Furthermore, the demodulation unit 140 may further comprise a synthetic waveform generator 141. In that case, the demodulation unit 140 may recover the modulating waveforms from the detection signal 132 by detecting the modulating frequencies of the detection signal 132 and generating analytic signals using the synthetic waveform generator 141 that produces sinusoidal waveforms with a fixed amplitude and the detected frequencies. This may be achieved according to an alternative option, according to which the modulating frequencies are not determined from the detection signal, but rather assumed to be known in advance. Additionally, the demodulation may involve multiplying the time-series of the pixel-values of the sensor 130 with the analytic signal formed from the modulating waveforms and computing the magnitude signal.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A system for determining a vital sign of a subject, said system comprising:
    two radiation sources for emitting differently modulated electromagnetic radiation with at least one equivalent wavelength onto a scene including the subject from different directions;
    a sensor for detecting electromagnetic radiation from the scene including the subject and for deriving a detection signal from the detected electromagnetic radiation;
    a demodulation unit configured to demodulate the detection signal to obtain two demodulated signals, each being demodulated differently using a demodulation corresponding to one of the modulations used for modulating the electromagnetic radiation emitted by one of said two radiation sources; and
    a processing unit for determining a vital sign of the subject by combining information from said two demodulated signals,
        wherein the processing unit is configured to demix the demodulated detection signals into a skin signal representing mainly electromagnetic radiation transmitted through or reflected from the skin of the subject and a non-skin signal representing mainly electromagnetic radiation not transmitted through or reflected from the skin of the subject, and
        wherein the processing unit is further configured to determine the vital sign of the subject from said skin signal.

2. The system according to claim 1, wherein the variations of said skin signal represent the vital sign.

3. The system according to claim 2,
    wherein the processing unit is configured to use a blind-source separation (BSS) to demix the demodulated detection signals into a skin signal and non-skin signal; and
    wherein the skin signal is selected by use of a quality metric.

4. The system according to claim 3,
    wherein the radiation elements of both radiation sources are the same, all radiation elements are configured to emit differently modulated electromagnetic radiation, the demodulation unit is configured to demodulate the detection signals detected by the sensor to obtain demodulated signals,
    wherein each demodulated signal is derived from electromagnetic radiation emitted by one radiation element, and
    wherein the processing unit is configured to combine skin signals corresponding to electromagnetic radiation emitted with one sub-spectrum by the radiation elements with skin signals corresponding to electromagnetic radiation with another sub-spectrum emitted by the radiation elements by using any of the multi-spectral pulse separation methods such as a chrominance based method, CHROM, blood volume pulse signature-based method, PBV, plane orthogonal to skin method, POS, or adaptive blood volume pulse method, APBV, to extract a vital sign from the skin signals.

5. The system according to claim 3, wherein the blind-source separation is at least one of Independent Component Analysis (ICA) or Principal Component Analysis (PCA).

6. The system according to claim 3, wherein the quality metric is at least one of spectral flatness, skewness, highest peak in normalized FFT spectrum or signal-to-noise ratio.

7. The system according to claim 1, wherein the radiation sources are configured to emit electromagnetic radiation in a range from 400 nm to 1000 nm.

8. The system according to claim 1, wherein the radiation sources each comprise one or more radiation elements to emit electromagnetic radiation with sub-spectra.

9. The system according to claim 1,
    wherein the radiation sources are configured to emit amplitude modulated electromagnetic radiation; and
    wherein the amplitude modulation of each radiation source uses a different frequency and/or phase modulation.

10. The system according to claim 9, wherein the radiation sources are configured to emit electromagnetic radiation that are modulated with the same frequency, but a different phase.

11. The system according to claim 9,
    wherein the demodulation unit further comprises includes a synthetic waveform generator;
    wherein the radiation sources are frequency multiplexed with sinusoidal waveforms; and
    wherein the demodulation unit is configured to recover the modulating waveforms from the detection signal by detecting the modulating frequencies of the detection signal and generating analytic signals using the synthetic waveform generator that produces sinusoidal waveforms with a fixed amplitude and the detected frequencies.

12. The system according to claim 1,
    wherein the sensor for detecting the electromagnetic radiation is a camera;
    wherein the two radiation sources are configured to emit differently modulated electromagnetic radiation using different modulating frequencies that differ more than the maximum frequency of a periodic vital sign, and
    wherein the highest modulating frequency is less than half the picture-rate of the sensor minus the maximum anticipated pulse-rate.

13. The system according to claim 1, wherein the demodulation unit comprises one or more amplitude modulated demodulators configured to output a number of output signals according to the number of radiation sources.

14. The system according to claim 1,
    wherein the demodulating unit is further configured to normalize and/or band-pass filter the demodulated signal to limit the frequency range of the demodulated signal to the relevant frequencies of the determined vital sign; and
    wherein normalization of the demodulated signal involves dividing each signal by its temporal mean or taking a logarithm of the demodulated signal.

15. A method for extracting a vital sign of a subject, said method comprising:
    emitting differently modulated electromagnetic radiation with at least one equivalent wavelength onto a scene including the subject from different directions by two radiation sources, detecting electromagnetic radiation from the scene including the subject and deriving a detection signal from the detected electromagnetic radiation, demodulating the detection signal to obtain two demodulated signals, each demodulated signal being demodulated differently using a demodulation corresponding to one of the modulations used for modulating the electromagnetic radiation emitted by one of said two radiation sources, and determining a vital sign of the subject by combining information from said two demodulated signals including demixing the demodulated detection signals into a skin signal representing mainly electromagnetic radiation transmitted through or reflected from the skin of the subject and a non-skin signal representing mainly electromagnetic radiation not transmitted through or reflected from the skin of the subject, and determining the vital sign of the subject from said skin signal.

* * * * *